US012661958B2

(12) United States Patent
Eynon et al.

(10) Patent No.: US 12,661,958 B2
(45) Date of Patent: Jun. 23, 2026

(54) HANDS-FREE CABIN PURIFICATION SYSTEM FOR A VEHICLE

(71) Applicant: FCA US LLC, Auburn Hills, MI (US)

(72) Inventors: Stephen J Eynon, New Baltimore, MI (US); Jason C Hedlund, West Bloomfield, MI (US); Danja McGoff, Washington Township, MI (US); Steven C Hall, Livonia, MI (US); Santiago Caceres, Pontiac, MI (US); Martin Hofmann, Ginsheim-Gustavsburg (DE); Richard S Silbert, Bingham Farms, MI (US); Mark D Osterbrink, Rochester Hills, MI (US); Edward Rickettson, Davisburg, MI (US)

(73) Assignee: FCA US LLC, Auburn Hills, MI (US)

( * ) Notice: Subject to any disclaimer, the term of this patent is extended or adjusted under 35 U.S.C. 154(b) by 576 days.

(21) Appl. No.: 18/191,122

(22) Filed: Mar. 28, 2023

(65) Prior Publication Data

US 2024/0326564 A1 Oct. 3, 2024

(51) Int. Cl.
B60H 3/00 (2006.01)
A61L 9/20 (2006.01)

(52) U.S. Cl.
CPC ............ B60H 3/0085 (2013.01); A61L 9/205 (2013.01); A61L 2209/12 (2013.01)

(58) Field of Classification Search
CPC ................ B60H 3/0078; B60H 3/0085; B60H 2003/0675
See application file for complete search history.

(56) References Cited

U.S. PATENT DOCUMENTS

| | | | |
|---|---|---|---|
| 8,221,679 B2 | 7/2012 | Golkowski | |
| 8,758,681 B2 | 6/2014 | Golkowski | |
| RE47,582 E | 8/2019 | Golkowski | |
| 2008/0053643 A1 | 3/2008 | Takagi et al. | |
| 2021/0077652 A1* | 3/2021 | Kim .......................... | F24F 8/22 |
| 2021/0346841 A1* | 11/2021 | Pujar ...................... | F24F 8/167 |

(Continued)

FOREIGN PATENT DOCUMENTS

| | | |
|---|---|---|
| CN | 101850706 B | 5/2012 |
| CN | 203727245 U | 7/2014 |

(Continued)

OTHER PUBLICATIONS

KR20150116800 and translation (Year: 2015).*

*Primary Examiner* — Steven S Anderson, II
(74) *Attorney, Agent, or Firm* — Jeremy J. Klobucar

(57) ABSTRACT

A cabin purification system for a vehicle includes an air inlet in communication with a fan, a light source emitting ultraviolet C light at a wavelength of from 100 nanometers to 280 nanometers, a photocatalytic oxidizer element, and an air outlet. The photocatalytic oxidizer element has a surface coating comprising anatase and rutile forms of $TiO_2$. The surface coating is illuminated by the light source. The fan generates an air flow from outside the air inlet to the air outlet. The air flow passes the light source and the photocatalytic oxidizer where the surface coating converts $H_2O$ $O_3$ and $O_2$ in the air flow into $H_2O_2$ which is distributed into the vehicle cabin to purify it.

20 Claims, 6 Drawing Sheets

(56)         References Cited

U.S. PATENT DOCUMENTS

| 2022/0260267 | A1 | | 8/2022 | Hipp | |
| 2022/0296765 | A1 | * | 9/2022 | Villamagna | ............. C23C 4/129 |

FOREIGN PATENT DOCUMENTS

| CN | 110373279 | A | | 10/2019 | |
| CN | 213007513 | U | | 4/2021 | |
| CN | 213442001 | U | | 6/2021 | |
| CN | 113427976 | A | | 9/2021 | |
| CN | 214874141 | U | | 11/2021 | |
| CN | 215938417 | U | | 3/2022 | |
| CN | 216636096 | U | | 5/2022 | |
| DE | 202021100771 | U1 | | 3/2021 | |
| JP | 2008064343 | A | | 3/2008 | |
| JP | 4285313 | B2 | | 6/2009 | |
| JP | 4379242 | B2 | | 12/2009 | |
| JP | 2018177055 | A | | 11/2018 | |
| KR | 20150116800 | A | * | 10/2015 | ........... B60H 3/0071 |
| WO | WO2017104369 | A1 | | 6/2017 | |

* cited by examiner

HANDS-FREE CABIN PURIFICATION SYSTEM FOR A VEHICLE

FIELD

The present disclosure relates to a hands-free system to purify a vehicle cabin space that does not require any user input or manipulation to operate.

BACKGROUND

People entering a vehicle may bring in pathogens with them either on their person or in the air they exhale. Other sources of pathogens may include animals, luggage, food and beverages brought into the vehicle and the cabin heating, ventilation and air conditioning (HVAC) system. Many of these pathogens are not able to be filtered by standard filters commonly found in HVAC systems. Currently there is no efficient way to purify the cabin space that does not require hands on work by a user to wipe down surfaces with a disinfectant, for example, but this takes times both to do and for the cleaning agent to work. As a normal cabin HVAC system circulates the cabin air and purges the air, it can thereby expose the cabin occupants to these pathogens.

Many pathogens, such as coronavirus COVID-19 (CV19), are not filtered by HEPA filters and they can settle onto surfaces in addition to passing through the air. Users are often uncomfortable adding chemical disinfectants such as Lysol and quaternary ammonium amines to their environmental space and they do not like to engage in the extensive cleaning required when using these chemicals. Current ultraviolet (UV) lights are not practical for treating cabin spaces due to safety concerns with their output and their need to be used in line-of-sight installations to be effective against pathogens.

SUMMARY

In at least some implementations, a cabin purifying system for a vehicle includes an air intake in communication with a fan; a first light emitting diode array emitting ultraviolet C light at a wavelength of from 100 nanometers (nm) to 280 nm; a first photocatalytic oxidizer element having a hydrophilic surface coating comprising anatase and rutile forms of $TiO_2$ with at least some of the surface coating illuminated by the first light emitting diode array; and an air outlet. The fan is configured to generate an air flow from outside the air intake to the air outlet and the surface coating of the first photocatalytic oxidizer element catalyzes the conversion of $H_2O$, $O_3$ and $O_2$ in the air flow into $H_2O_2$.

In at least some implementations, more than 50% of the total amount of $TiO_2$ in the surface coating is in the anatase form.

In at least some implementations, the surface coating further includes at least one transition metal element from the Periodic Table.

In at least some implementations, the at least one transition metal element comprises zinc.

In at least some implementations, the first photocatalytic oxidizer element comprises at least two panels at an angle relative to each other.

In at least some implementations, the system further includes a second light emitting diode array emitting ultraviolet A light at a wavelength of from 315 nm to 400 nm and a second photocatalytic oxidizer element having a surface coating comprising anatase and rutile forms of $TiO_2$, the surface coating of the second photocatalytic oxidizer illuminated by the second light emitting diode array and the second photocatalytic oxidizer element catalyzing the oxidation of volatile organic compounds in the air flow.

In at least some implementations, the second photocatalytic oxidizer element comprises a gridwork having multiple openings in the gridwork and the gridwork is covered by the surface coating.

In at least some implementations, each of the plurality of openings has an inlet and an outlet relative to the air flow and a diameter of the inlet of at least some of the openings is smaller than a diameter of the outlet of those openings.

In at least some implementations, the second light emitting diode array is at an angle of up to 30 degrees relative to a parallel orientation to the second photocatalytic oxidizer element.

In at least some implementations, the first and the second photocatalytic oxidizer elements are arranged in series.

In at least some implementations, a cabin purifying system for a vehicle includes: an air intake in communication with a fan; multiple light emitting diode arrays, with at least one of the light emitting diode arrays emitting ultraviolet C light at a wavelength of from 100 nm to 280 nm and at least one of the light emitting diode arrays emitting ultraviolet A light at a wavelength of from 315 nm to 400 nm; multiple photocatalytic oxidizer elements, each having a surface coating comprising $TiO_2$, with the surface coating of at least one of the photocatalytic oxidizer elements illuminated by at least one of the light emitting diode arrays emitting ultraviolet C light at a wavelength of from 100 nm to 280 nm and with the surface coating of at least one of the photocatalytic oxidizer elements illuminated by at least one of the light emitting diode arrays emitting ultraviolet A light at a wavelength of from 315 nm to 400 nm; an air outlet; a control module, the control module controlling the fan and each of the light emitting diode arrays. The fan is configured to generate an air flow into and through the air intake to the air outlet and the surface coating illuminated by ultraviolet C light catalyzes the conversion of $H_2O$, $O_3$ and $O_2$ in the air flow into $H_2O_2$ and the surface coating illuminated by ultraviolet A light catalyzes the oxidation of volatile organic compounds in the air flow.

In at least some implementations, the photocatalytic oxidizer elements are arranged in series.

In at least some implementations, each of the photocatalytic oxidizer elements having a surface coating illuminated by ultraviolet C light comprises a metal substrate having the surface coating applied thereon.

In at least some implementations, at least some of the ultraviolet light emitted by at least one of the light emitting diode arrays is reflected by a reflector comprising polytetrafluoroethylene.

In at least some implementations, the surface coating comprises greater than 50% of the $TiO_2$ in an anatase form.

In at least some implementations, the surface coating illuminated by ultraviolet C light is hydrophilic.

In at least some implementations, the surface coating illuminated by ultraviolet A light is hydrophobic.

In at least some implementations, the control module receives inputs regarding at least one of a humidity and a temperature of air in the air flow entering the air inlet and adjusts at least one of a speed of the fan and a power output to at least one of the light emitting diode arrays based on the at least one of the humidity and the temperature.

In at least some implementations, the photocatalytic oxidizer element illuminated by at least one of the light emitting diode arrays emitting ultraviolet A light comprises a gridwork having a plurality of openings in the gridwork and the gridwork is covered by the surface coating.

In at least some implementations, each of the plurality of openings has an inlet and an outlet relative to the air flow and a diameter of the inlet of at least some of said openings is smaller than a diameter of the outlet of said openings.

Further areas of applicability of the present disclosure will become apparent from the detailed description, claims and drawings provided hereinafter. It should be understood that the summary and detailed description, including the disclosed embodiments and drawings, are merely exemplary in nature intended for purposes of illustration only and are not intended to limit the scope of the invention, its application or use. Thus, variations that do not depart from the gist of the disclosure are intended to be within the scope of the invention.

DETAILED DESCRIPTION

Figure 1:
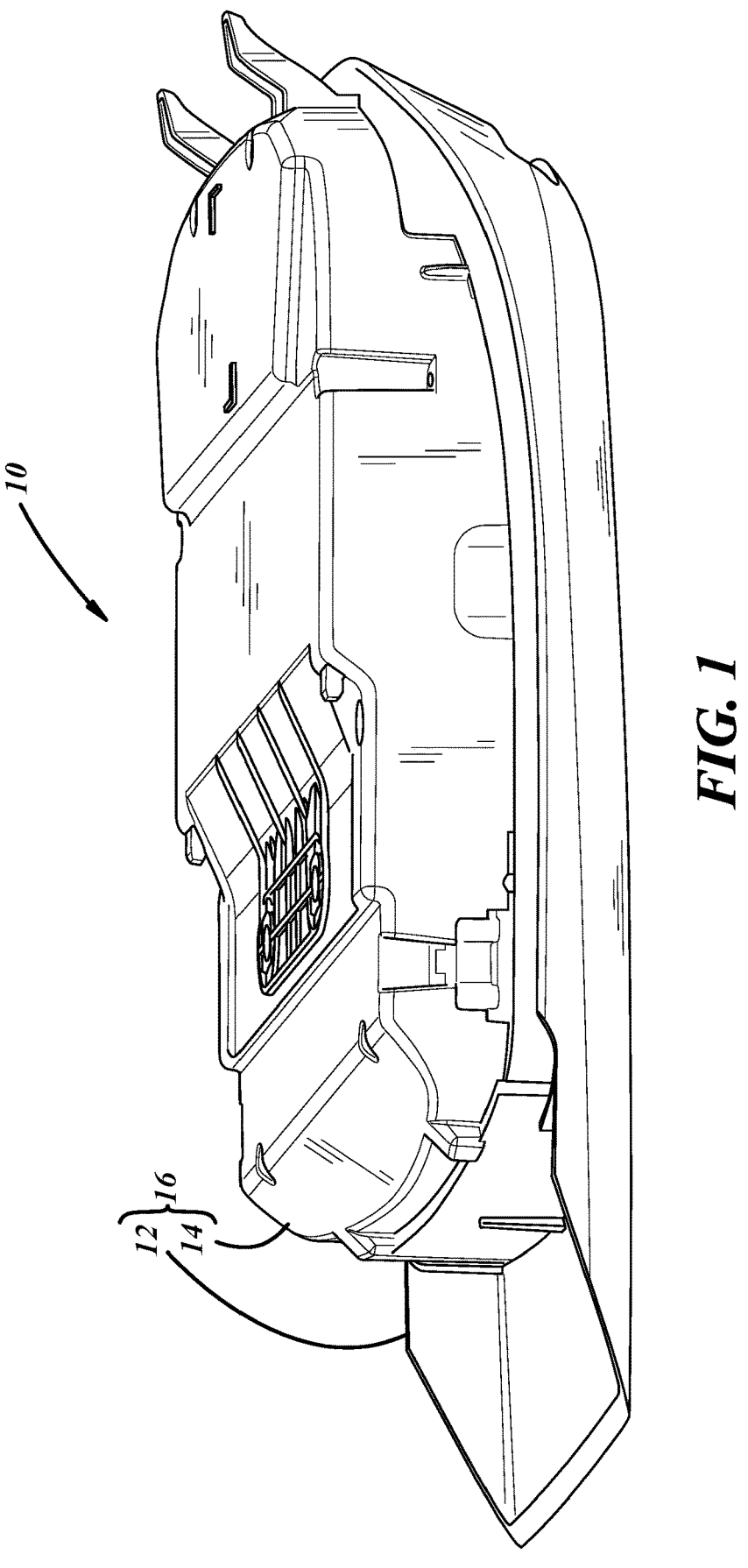
FIG. 1 is a perspective view of an overhead console including one implementation of a cabin purifying system.

The disclosure is directed to a hands-free purifying system for a vehicle to treat the cabin space for, for example, pathogens including viruses, bacteria, mold, fungus and fungal spores. As an overview, the system includes one or more fans to draw in cabin air and direct air through a series of photocatalytic oxidizing (PCO) elements which are activated by exposure to UV light generated by light emitting diode (LED) arrays in the system. Air including purifying agents from the PCO elements is then discharged into the cabin space to purify the cabin space. In at least some implementations, the output air flow from the system is directed into an inhalation zone of the cabin, to maximize efficacy. The inhalation zone of a cabin is generally defined as the area from the floor to the headliner of the cabin and more preferably from the seat cushion level to the headliner of the cabin.

Multiple LED arrays may be used and they may be tuned to emit ultraviolet light at different wavelengths. In at least some implementations, one or more LED arrays emit light in the UV-A range at a wavelength of from 315 nanometers (nm) to 400 nm, and each such array is referred to herein as a UV-A LED array. One or more LED arrays may be tuned to emit ultraviolet light in the UV-C range at a wavelength of from 100 nm to 280 nm, and each such array is referred to herein as a UV-C LED array.

In at least some implementations, different types of PCO elements may be used to catalyze different reactions, as noted herein. For example, one type of PCO element catalyzes the conversion of water ($H_2O$), ozone ($O_3$) and oxygen ($O_2$) in the air into hydrogen peroxide ($H_2O_2$) which is then passed into the cabin space. These PCO elements may be tuned to be activated by one or more UV-C LED arrays and are referred to as PCO-C elements. Another type of PCO element may be tuned to be activated by one or more UV-A LED arrays and are referred to as PCO-A elements. The PCO-A elements catalyze the oxidation of volatile organic compounds (VOCs) in the airflow to reduce the level of VOCs in the cabin air flow. The UV-A LED arrays in combination with the PCO-A elements continuously oxidize VOCs in the air flow. In addition, the UV-A LED arrays can purify the air flow of some pathogens by time-of-flight destruction of the pathogens. This form of purifying the air flow of pathogens can be especially important when the air humidity is below 5% relative humidity as at those humidity levels the conversion of water, ozone and oxygen into hydrogen peroxide by the PCO-C elements is less efficient. In addition, the UV-C LED arrays could be used to oxidize the VOCs in the air flow when their light is directed to a photocatalytic oxidizer element tuned to catalyze this oxidation reaction; however, current cost considerations make use of UV-A LED arrays more cost-effective for the oxidation of VOCs.

The $H_2O_2$ discharged by the system acts as a non-selective bactericidal and antiviral agent that can destroy the pathogens in the air and on the cabin surfaces. Levels of 5 parts per billion (ppb) or more of $H_2O_2$ can be reached in the cabin space within several minutes by the system, dependent on the air humidity and temperature. The $H_2O_2$ can also settle into soft surfaces of the cabin such as carpets, headliners and seats and then once saturated therein, which can take as little as 20 minutes, $H_2O_2$ will continue to be off gassed from these $H_2O_2$ "capacitor" sites into the cabin even after the purifying system is turned off and when the system is purged. The $H_2O_2$ can also land on and purify trim panels, dashes, consoles and other cabin surfaces. Thus, the system can achieve effective pseudo steady state levels of $H_2O_2$ in the parts per billion (PPB) in a vehicle cabin to effectively purify the cabin space in a hands-free manner.

Referring in more detail to the drawings, FIG. 1 is a perspective view of an overhead console implementation of a cabin purification system shown generally at 10. This implementation includes a lower housing 12 secured to an upper housing 14 to form an outer housing 16. The system 10 in this implementation may be installed into an overhead console location in a vehicle cabin, although the system may be located in different areas of the vehicle, as desired.

Figure 2:
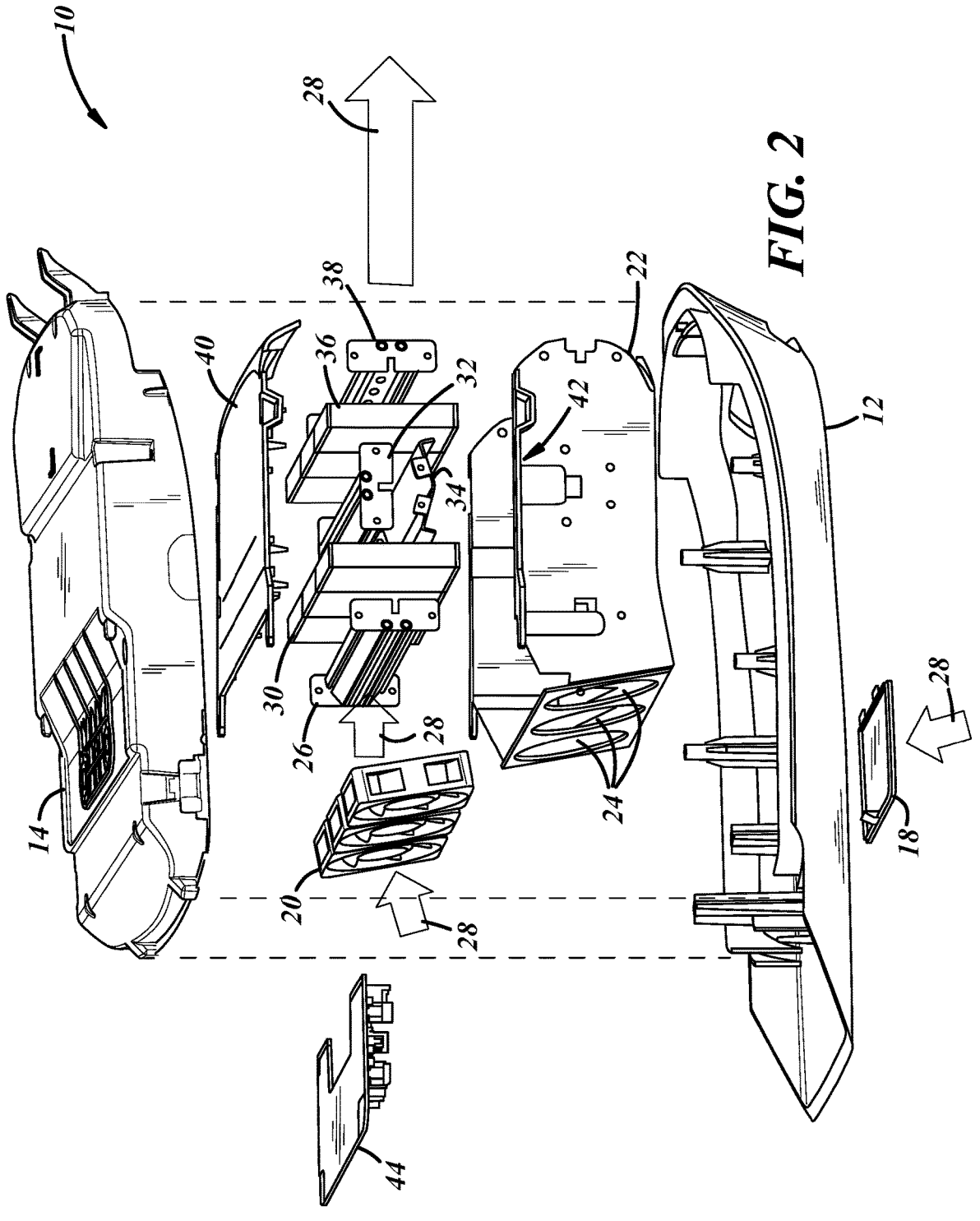
FIG. 2 is an exploded view of the purifying system shown in FIG. 1.

FIG. 2 is an exploded perspective view of the system 10 as shown in FIG. 1. The lower housing 12 includes an air intake 18 through which air is drawn into the system 10 by an air mover, which may include or be defined by one or more fans 20. The air intake 18 can include a replaceable air filter, such as a HEPA filter (not shown) incorporated into the air intake 18. The fans 20 are mounted to a housing 22 having a series of inlets 24 that align with the fans 20.

Mounted inside the housing 22 and within an air flow 28 generated by the fans 20, are one or more LED arrays and PCO elements. In the example shown, the housing 22 contains at least part of a first light emitting diode (LED) array 26, a first PCO element 30, a second LED array 32, a second PCO element 34, a third PCO element 36, and a third LED array 38. The first LED array 26 is designed to allow the air flow 28 from the fans 20 to pass through and around it, and the first LED array 26 is located downstream of the fans 20 and emits UV light in the A range (UV-A), such as at a wavelength of from 315 nm to 400 nm. Thus, the first LED array 26 is a UV-A LED array.

In series with and downstream from the first LED array 26 is the first photocatalytic oxidizer (PCO) element 30. The first PCO element 30 has a surface coating, described herein below, that is activated by the first LED array 26 to catalyze the oxidation of VOCs in the air flow 28. In series with the first PCO element 30 is a second LED array 32 that emits UV-C light at a wavelength of from 100 nm to 280 nm. Mounted below the second LED array 32 is the second PCO element 34 having a surface coating, described herein below, that is activated by the second LED array 32 to catalyze the conversion of water, ozone and oxygen in the air flow 28 into hydrogen peroxide.

The third PCO element 36 is located in series with the second LED array 32 and second PCO element 34. The third PCO element 36 may be constructed the same as the first PCO element 30 and is activated by the third LED array 38, which emits UV-A light at a wavelength of from 315 nm to 400 nm. The third LED array 38 is located in series with the third PCO element 36.

Figure 3:
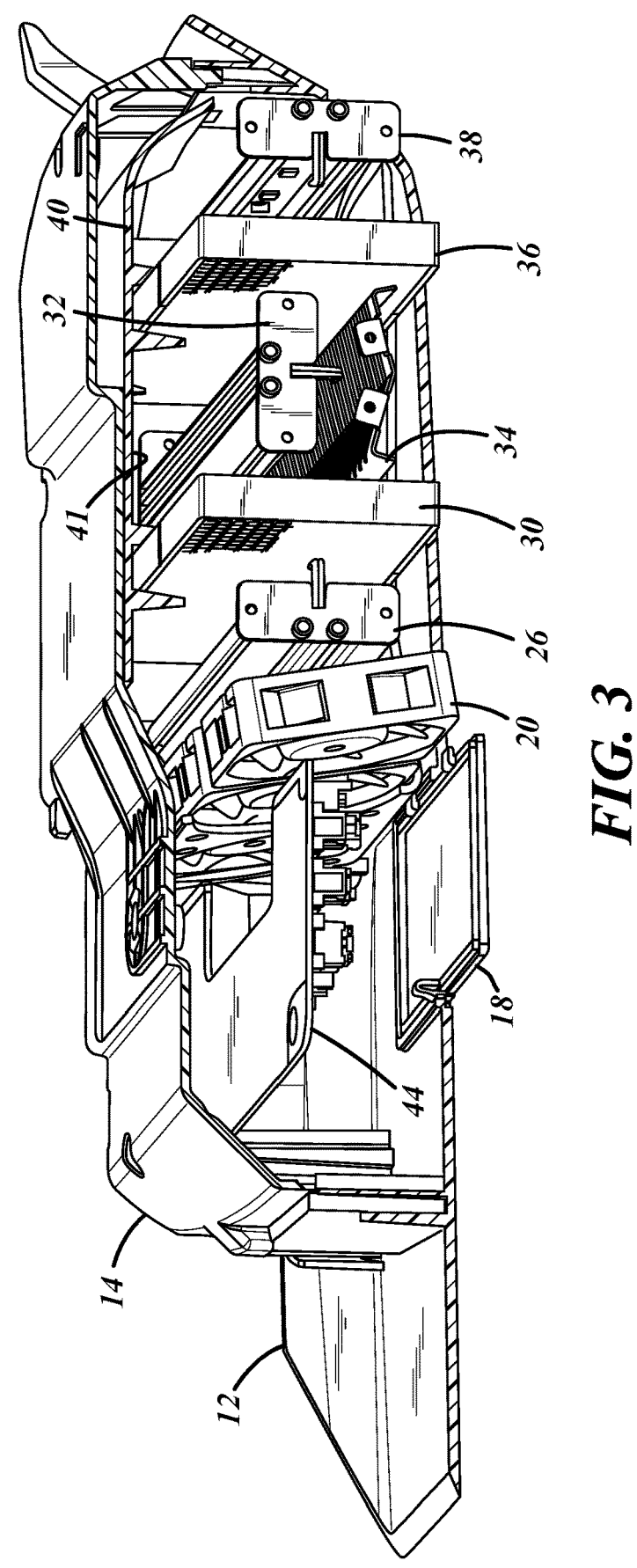
FIG. 3 is a cut-away view of the purifying system shown in FIG. 1.

An air deflector 40 is fitted to a top rim 42 of the housing 22 above and overlying the first LED array 26, first PCO element 30, second LED array 32, second PCO element 34, third PCO element 36 and third LED array 38. On an underside of the deflector 40 is a UV light reflector 41 that reflects the UV light from at least one of the LED arrays 26, 32 and 38 onto at least one of the PCO elements 30, 34, 36. Preferably the UV light reflector 41 is positioned to reflect the light from at least the UV-C LED array 32 and is described in further detail below. The system 10 may further include a control module 44 to control the fans 20 and the LED arrays 26, 32, and 38. FIG. 3 is a cut away view of FIG. 1 wherein the outer housing 16 has been cut along the longitudinal centerline of the outer housing 16 and shows the components of the system 10 in situ in the outer housing 16.

Figures 4, 5, 8:
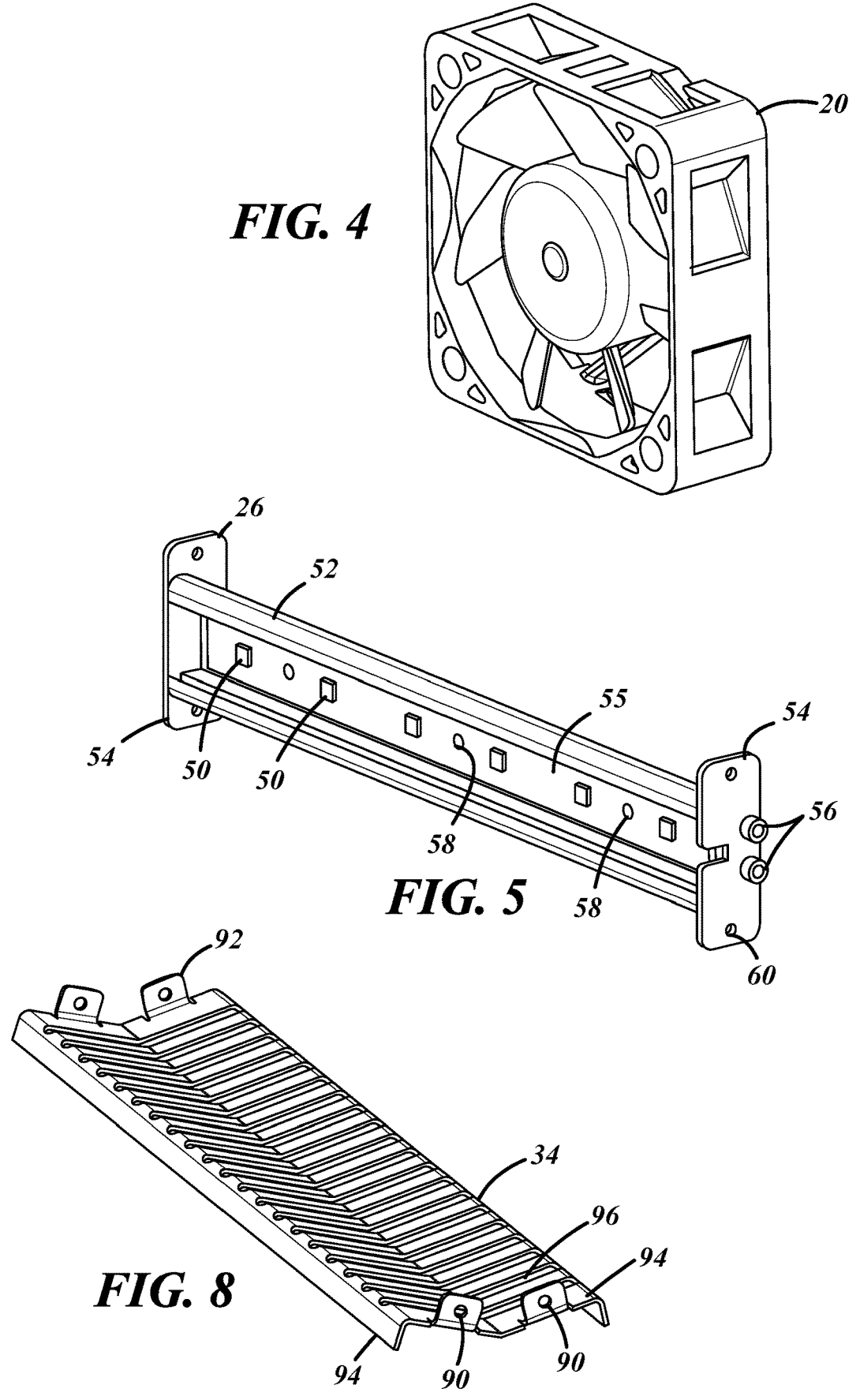
FIG. 4 is perspective view of a fan that may be used in the purifying system.
FIG. 5 is a perspective view of a light emitting diode array that may be used in the purifying system.
FIG. 8 is perspective view of a photocatalytic oxidizer element that is activated by ultraviolet light and that may be used in the purifying system.

FIG. 4 shows a perspective view of one of the fans 20 of the system 10, that includes vanes mounted to a hub that is in turn mounted for rotation about a central axis, and which may be driven by a motor. FIG. 5 shows a perspective view of the first LED array 26, which, in the illustrated example, is the same design as the third LED array 38, both of which emit UV-A light at a wavelength of from 315 nm to 400 nm. The first LED array 26 includes a series of LEDs 50 spaced along the length of a support frame 52 having two end caps 54 and a body 55 between and coupled to the end caps. Each end cap 54 includes a mounting structure which may be mounting screws 56 as shown to mount the body 55 including the LED array 26 to the end caps 54. Other mounting structures can be used to mount the LED array 26 and body 55 to the end caps 54. To allow air flow through the LED array 26, the body 55 may include a series of openings 58 formed therethrough, extending through a front surface facing the fans 20 and an opposite rear surface. The front surface may be generally perpendicular to the direction of air flow 28 from the fans, where generally perpendicular includes perpendicular and orientations within 30 degrees of perpendicular. To enable further air flow, space may be provided between an upper surface of the frame 52 and the reflector 40, and further space may be provided between a lower surface of the frame 52 to a bottom wall of the housing 22 so that air may flow over and under the frame 52. The end caps 54 include openings 60 to allow the LED array 26 to be mounted to the housing 22 by fasteners, although other arrangements may be used, including receipt of the end caps 54 in grooves or channels of the housing 22.

Figure 6:
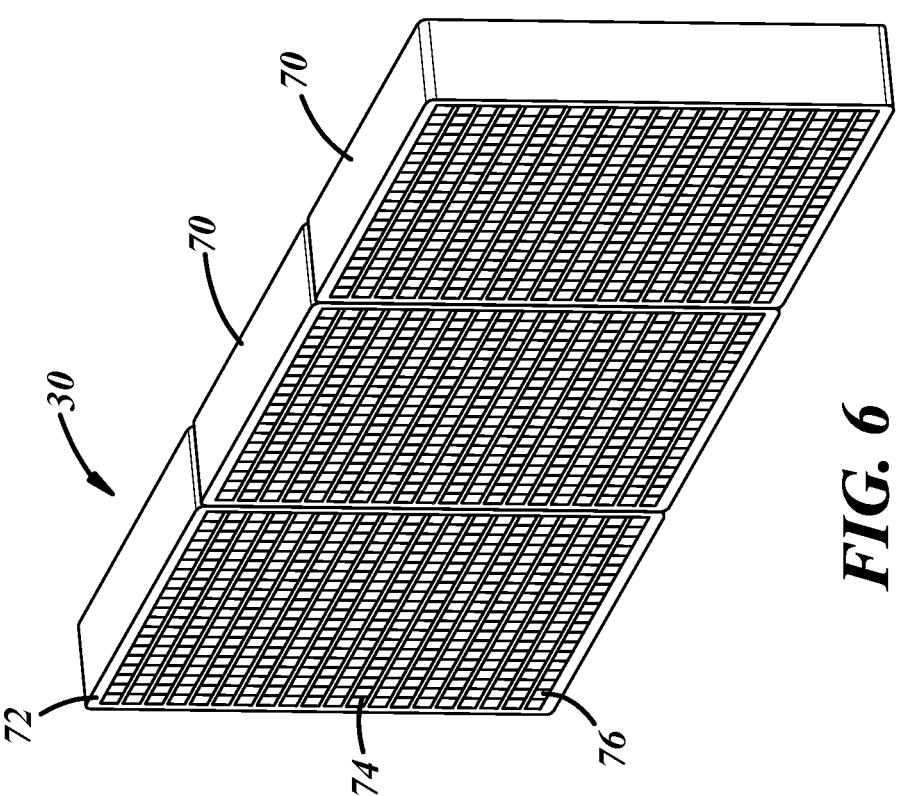
FIG. 6 is a perspective view of a photocatalytic oxidizer element that is activated by ultraviolet light and that may be used in the purifying system.

FIG. 6 shows a perspective view of the first PCO element 30, and in the illustrated implementation the third PCO element 36 has the same structure as described herein. In at least one implementation, the first PCO element 30 includes a series of panels 70 each having an outer frame 72 and an internal gridwork 74 having a plurality of openings 76 that pass through the panel 70. The openings 76 can have any desired shape. At least some and up to the entire internal gridwork 74 of each panel 70 is coated with a photocatalytic oxidizer surface coating, as described herein, that is tuned to be activated by the UV-A light from the first LED array 26. In at least some implementations, the panels 70 may be oriented so that a front face of each faces toward the rear surface of the support frame body of the LED array, and a rear face of the panels faces toward the second LED array 32. The front and rear faces of the panels 70 may be generally parallel (i.e. parallel or within 30 degrees thereof) to each other and to the front and rear surfaces of the first LED array. So arranged, air flows into the panels at the front face and exits the panels at the rear face. The third PCO element 36 may be constructed, arranged and activated by the third LED array 38 in the same way, with the third PCO element 36 arranged downstream of the second LED array 32 and upstream of the third LED array 38, as noted above.

Figure 7:
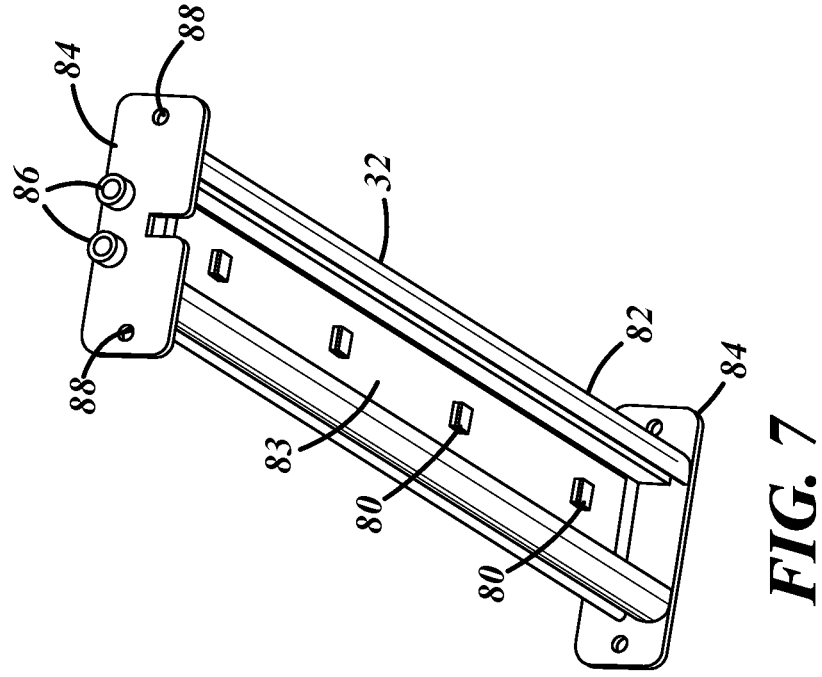
FIG. 7 is a perspective view of another light emitting diode array that may be used in the purifying system.

FIG. 7 is a perspective view of the second LED array 32. The second LED array 32 includes a series of LEDs 80 spaced along the length of a support frame 82 having a body 83 and end caps 84 at opposite ends of the body 83. These LEDs 80 emit light in the UV-C range at a wavelength of from 100 nm to 280 nm. Each end cap 84 includes a mounting structure which may be mounting screws 86 as shown to mount the LED array 32 and body 83 to the end caps 84. Other mounting structures can be used to mount the LED array 32 and support frame 82 to the end caps 84. Each end cap 84 includes openings 88 to mount the LED array 32 to the housing 22 by fasteners, although other arrangements may be used, including receipt of the end caps 54 in grooves or channels of the housing 22. In at least some implementations, as shown in FIG. 3, the second LED array 32 may be arranged generally perpendicular (i.e. perpendicular or within 30 degrees thereof) to the first LED array 26 and the first PCO element 30. In this way, the openings 88 extend through an upper surface that faces toward the reflector 40 and an opposite lower surface that faces the bottom wall of the housing. Air may flow over the upper and lower surfaces of the support frame body 83.

FIG. 8 is a perspective view of the second PCO element 34, which is tuned to be activated by the UV-C light emitted by the second LED array 32 in the system 10. The second PCO element 34 includes a series of openings 90 on tabs 92 to allow it to be mounted to the housing 22. The second PCO element 34 can be configured as a single M shaped sheet with two panels 94 at an angle to each other as shown. The panels 94 include openings (e.g. slots 96) to allow for air flow. And the panels may be oriented similarly to the second LED array, with an upper surface facing towards the lower surface of the second LED array, and a lower surface facing toward the bottom wall of the housing 22. The second PCO element 34 is covered with a photocatalytic oxidizer surface coating, described herein below, tuned to be activated by the second LED array 32 emitting UV-C light.

The air deflector 40, as described, preferably on its underside includes a UV light reflector 41. The UV light reflector 41 may comprise any of a variety of UV light reflective materials. In one embodiment it may comprise a coating of polytetrafluoroethylene (PTFE), a common brand being Teflon®, secured to the underside of the air deflector 40 to reflect at least some of the UV-A and/or UV-C light emitted by the LED arrays 26, 32, 38. The PTFE is especially useful as a UV light reflector material since it is chemically inert, it can be molded, it is not damaged by UV light, it has a very high reflectance of UV light, and it can cause a diffuse reflection, approaching Lambertian reflectance, to the PCO elements 30, 34, 36. Also the PTFE is hydrophobic and so it will not adsorb water from the air flow 28 passing over it. In another implementation the entire UV light reflector 41 can be formed from PTFE rather than just comprising a coating of PTFE. The coating of PTFE can be applied to a pressure sensitive adhesive tape that is then applied to the air deflector 40 in some embodiments. The PTFE coating or structure may comprise a microporous PTFE having a thickness of about 1.1 millimeters to 0.7 millimeters. Alternatively, the UV reflector 41 could comprise roller side aluminum foil that is coated with PTFE. In another embodiment the UV light reflector 41 could comprise roller side anodized aluminum foil. In other embodiments the UV light reflector 41 can comprise polished stainless steel. In other embodiments, the UV light reflector 41 can comprise aluminum vacuum metalized and UV coated acrylonitrile butadiene styrene (ABS), acrylonitrile styrene acrylate (ASA), polycarbonate (PC), or combinations of ABS/PC or ASA/PC. The UV light reflector 41 could alternatively be positioned under one or more of the LED arrays 26, 32, 38 rather than or in addition to being above them. In other embodiments, the UV light reflector 41 could be positioned to reflect only the UV-A light, only the UV-C light, or any combination thereof.

Figure 9:
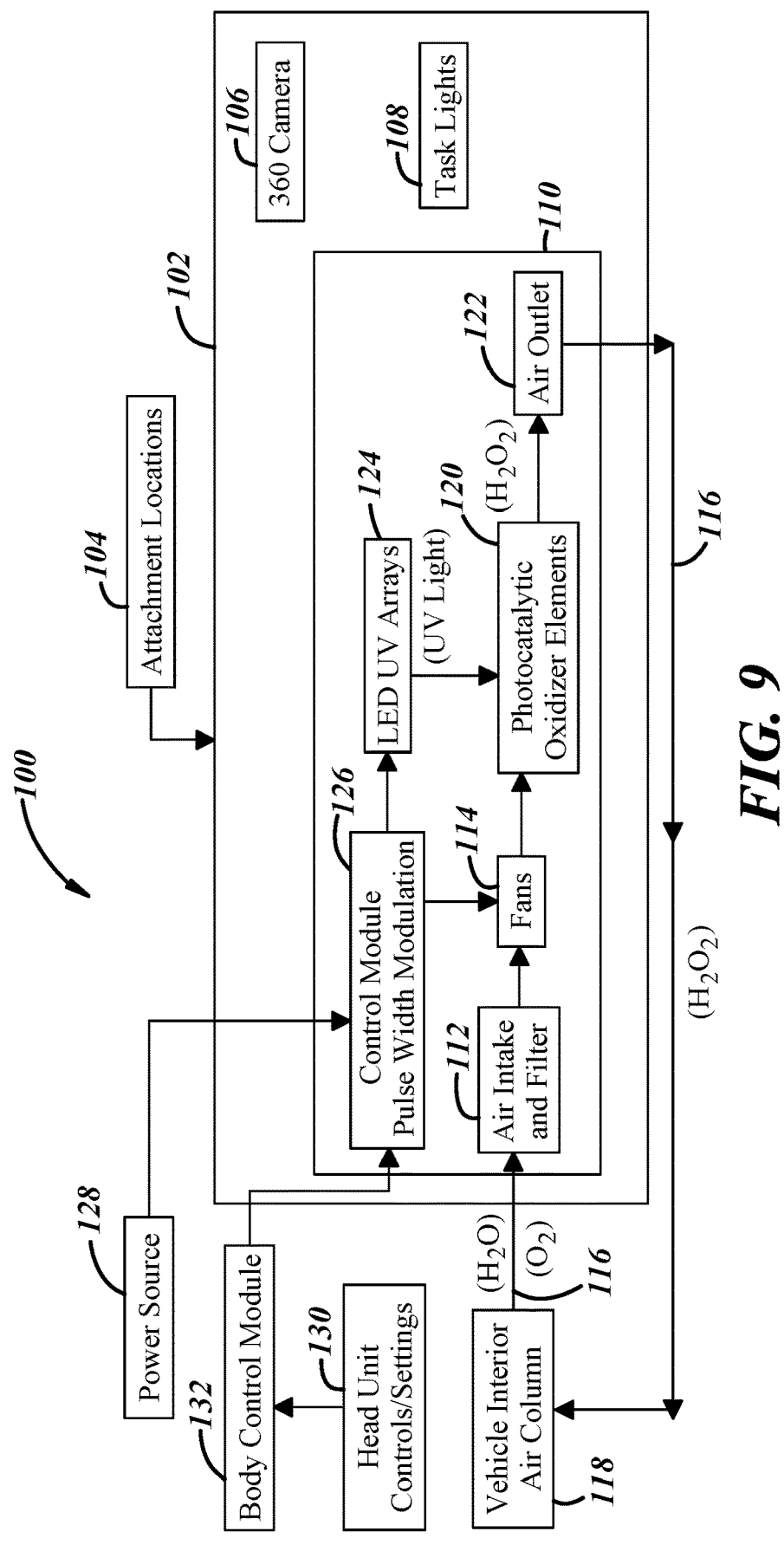
FIG. 9 is a block diagram of a purifying system.

FIG. 9 is a block diagram 100 of the system 10 such as may be provided in an overhead console as shown in FIG. 1, or elsewhere in the vehicle. In this example, an overhead console 102 includes a series of attachment locations 104 to secure it in an overhead location in the cabin. The overhead console 102 may include a camera feature 106, which may have a 360-degree Field of view, and often includes task lighting 108. The overhead console 102 further includes a cabin purification system 110.

The cabin purification system 110 includes an air intake and filter 112 to filter out gross size particles in the size range of 20 to 40 microns. Fans 114 create an air flow 116 through the purification system 110 by drawing air from a vehicle interior air column 118, meaning the air in the cabin outside the system 110, in through the air intake and filter 112 and pushing it through PCO elements 120 and out into the cabin interior through an air outlet 122. The PCO elements 120 are illuminated by LED arrays 124 emitting UV light at desired wavelengths as described herein. A control module 126 provides power to and regulates the fans 114 and the LED arrays 124. The control module 126 can provide pulse width modulation control.

The air flow 116 into the air intake and filter 112 contains $H_2O$, $O_3$, $O_2$, and VOCs along with other components and has a relative humidity, preferably ranging from 5% to 95%. One or more PCO elements 120, illuminated by the LED arrays 124, catalyze the formation of $H_2O_2$ from the input $H_2O$, $O_3$ and $O_2$. The air flow 116 out of the air outlet 122 and into the cabin space thus contains $H_2O_2$ which purifies the cabin air space and surfaces. One or more other PCO elements catalyze the oxidation of VOCs and the LED arrays illuminating them can also serve to provide time-in-flight destruction of pathogens. This alternative destruction of pathogens can be helpful especially when the air flow 28, 116 humidity is less than 5% relative humidity as formation of $H_2O_2$ is reduced at such low relative humidity. A power source 128 provides power to the control module 126 at a nominal voltage and amperage (e.g. 12 volts DC with a range of 10.5 to 16.5 volts DC at a range of 1.5 to 3.0 amps). The overhead console 102 also receives input from head unit controls and settings 130 through a body control module 132 which can include an on/off control switch to the control module 126 that can be operated by a user or can be controlled by the HVAC settings.

As described, the system 10, 110 draws in an air flow 28, 116 from the cabin space using one or more fans 20, 114 and this air flow 28, 116 comprises $H_2O$, $O_3$, $O_2$, VOCs and other air components at various levels including the pathogens. The system 10, 110 may include additional air intakes (not shown) that may be placed anywhere that is convenient, preferably at locations in the cabin with the highest air humidity such as the forward and/or aft glazing locations or near the floor of the vehicle to maintain the widest possible operating window of the system 10, 110 these other air intakes direct their air flow into the air intake 18 112 of the system 10, 110. The air flow 28, 116 is directed by the fans 20, 114 through the first LED array 26 emitting Ultraviolet A (UV-A) light and is then directed through a first PCO element 30. A surface coating, described herein, on the PCO element 30 is activated by the UV-A light and catalyzes the oxidation of VOCs in the air flow 28, 116. The UV-A LED arrays 26, 38 can also kill pathogens in a time-in-flight manner as described.

The air flow 28, 116 is then directed under the second LED array 32 emitting UV-C light which activates the surface coating on the second PCO element 34. The second PCO element 34 catalyzes the conversion of $H_2O$, $O_3$ and $O_2$ into $H_2O_2$, which is released into the cabin. The reactions are given below:

$$H_2O + O_3 \rightarrow H_2O_2 + O_2$$

$$2H_2O + O_2 \rightarrow 2H_2O_2$$

The air flow 28, 116 is then directed through a third PCO element 36 that is illuminated by a third LED array 38 emitting UV-A light. The third PCO element 36 and third LED array 38 function the same as the first LED array 26 and first PCO element 30. The air flow 28, 116 is then directed out of the system 10, 110 and into the cabin space. The air flow 28, 116 directed into the cabin now contains $H_2O_2$ in addition to $H_2O$, $O_3$, $O_2$, VOCs, and other air components with lower levels of $H_2O_2$, $O_3$, $O_2$ and VOCs than the inflow.

The system 10, 110 is controlled by a control module 44, 126 that uses algorithms to control the speed of the fans 20, 114 and power to the LED arrays 26, 32, 38, 124. The control module 44, 126 can receive inputs from sensors in the HVAC system that monitor the air humidity and temperature. These sensors are typically found at the windshield areas. The sensor inputs can be used to optimize the power settings of the system 10, 110 given the cabin air humidity and temperature. The average power usage ranges from 8 to 30 watts and the system 10, 110 is sized to the size of the cabin space. Alternatively, the system 10, 110 can be run as an open loop system with a single fan speed and no inputs from the vehicle sensors. In both examples a user controlled on/off switch may be incorporated into the system 10, 110 to allow a user to control the system 10, 110. Various elements of the system 10, 110 are further described below.

The first and third PCO elements 30, 36 include an internal gridwork 74 in the form of a grid, honeycomb pattern or any other desired pattern with a plurality of openings 76, having any desired shape, in the internal gridwork 74. The internal gridwork 74 is designed to maximize the surface area and the openings 76 allow for the air flow 28, 116 to pass through the PCO elements 30, 36. The openings 76 in the gridwork 74 can be designed to have smaller diameter inlets and larger (e.g. wider) diameter outlets relative to the direction of air flow 28, 116 to maximize air flow and the amount of active surface area exposed to the UV-A light from the LED arrays 26, 38. The gridwork 74 of the panels 70 is generally formed from a non-polar substrate such as a plastic material. The gridwork 74 is coated with a PCO surface coating comprising $TiO_2$. $TiO_2$ has at least three polymorphic forms: anatase, rutile, and brookite, with rutile being the most stable. The PCO surface coatings of all the PCO elements 30, 34, 36 in the present system 10, 110 comprise $TiO_2$ with the majority of it, meaning more than 50% of the total $TiO_2$ in the surface coating, in the anatase polymorphic form and the rest comprising the rutile form.

The anatase form of $TiO_2$ is very reactive, has a low cost and a high specific surface and thus is preferably the major form of $TiO_2$ in the PCO surface coatings. The rutile form of $TiO_2$ enhances the distribution of the anatase form and any transition metal elements in the surface coating, as described below, and increases the mechanical strength of the surface coating and contributes to antiaging properties of the surface coating. In addition, the rutile form of $TiO_2$ has some antibacterial activity. The mixture of anatase and rutile $TiO_2$ may be adjusted to maximize the catalytic conversion reactions at the wavelengths (e.g. UV-A or UV-C), of the light emitted from the UV LED arrays 26, 32, 38.

The photocatalytic oxidizer surface coatings of the first and third PCO elements 30, 36 may also include some synthetic zeolites to make them more hydrophobic and to encourage the water in the air flow 28, 116 to pass through them for use on the second PCO element 34. The photocatalytic oxidizer surface coatings on the first and third PCO elements 30, 36 are tuned to be activated by the first and third UV LED arrays 26, 38 to catalyze the oxidation of VOCs in the air flow 28, 116.

The $TiO_2$ containing photocatalytic oxidizer surface coating of the second PCO element 34 is designed to be hydrophilic and the hydrophilicity is increased by including natural as opposed to synthetic zeolites in the surface coating. The second PCO element 34 base substrate is generally a metal that the photocatalytic oxidizer surface coating is coated onto. The hydrophilicity of the surface coating is beneficial to the conversion reaction as it increases the $H_2O$ levels that can be adsorbed from the air flow 28, 116 passing through the system 10, 110. The PCO surface coating on the second PCO element 34 may also comprise transition metal elements from the Periodic Table. These transition metal elements can lower the activation energy for the conversion of $H_2O$, $O_3$ and $O_2$ into $H_2O_2$ and thus increase the efficiency of the second PCO element 34 at a lower power density input. The transition metal elements are also helpful when condensing levels of humidity are expected in the system 10, 110. Certain transition metal elements can also have antibacterial properties themselves further adding to the effectiveness of the system 10, 110. In one example zinc is used as the transition metal in a PCO element surface coating since it is more economical than silver, which can also be used. The surface coating of the second PCO element can also include the element Yttrium, which is a transition metal, fumed silica, $ZiO_2$ and $Al_2O_3$.

Suitable PCO elements 30, 34, 36, 120 with desired surface coatings are commercially available from a variety of sources including Extreme Microbial Technologies located in Dayton, Ohio USA or RGF Environmental Group, Inc. located in Riviera Beach, Florida, USA. Although the system 10, 110 is illustrated with the use of only three PCO elements 30, 34, 36 it is understood that additional PCO elements could be included in the system 10, 110 as require by the pathogen load and/or cabin space. Preferably the PCO elements 30, 34, 36, are placed in series to maximize the activation by the LED arrays 26, 32, 38 and to increase the efficiency of the system 10, 110.

In the system 10, 110 the UV-A emitting LED arrays 26, 38 emit UV-A light at a wavelength of from 315 nm to 400 nm and the UV-C LED array 32 emits UV-C light at a wavelength of from 100 nm to 280 nm. The UV-C LED array 32 activates the second PCO element 34 surface coating to catalyze the formation of $H_2O_2$ from the $H_2O$, $O_3$ and the $O_2$ in the air flow 28, 116. The UV-A LED arrays 26, 38 activate the first and second PCO elements 30, 36 to catalyze the oxidation of volatile organic compounds (VOCs) in the air and contributes to time-of-flight killing of pathogens in the air flow 28, 116. The UV-A LED arrays 26, 38 are shown as being parallel to the PCO elements 30 and 36 in the Figures; however, they can be tilted by up to 30 degrees toward or away from the PCO element 30, 36 relative to a parallel orientation to increase the surface area of the gridwork 74 exposed to the UV-A light and to thereby increase the activated surface area of the PCO elements 30, 36. Another way of expressing this that the UV-A LED arrays 26, 38 can be tilted at angle of up to 30 degrees relative to a face of the PCO element 30, 36. Tilting the UV-A LED arrays 26, 38 can increase the PCO element 30, 36 surface area exposed to the UV-A light by up to 22%. The LED arrays 26, 32, 38 124 can also be pulse width modulated by the control module 44, 126 to match the illumination output to the ambient humidity levels as detected in the air and to the composition of the PCO surface coating. Although three LED arrays 26, 32, 38 are sufficient to illuminate and activate three PCO elements 30, 34, 36, if the number of PCO elements 30, 34, 36 are increased then one could also increase the LED arrays 26, 32, 38 as necessary to illuminate and active the surface coatings of the additional PCO elements.

The UV-C and UV-A emitting LED arrays 26, 32, 38, 124 could be replaced with dielectric barrier discharge (DBD) excimer lamps coated with a UV phosphor to produce the desired UV-C or UV-A wavelengths of light. This solution, however, requires the use of high voltage ballasts which may be undesirable in a passenger vehicle, which are not found in the preferred LED arrays 26, 32, 38. The ballasts for the DBD excimer lamps could be integrated onto the control module 44 and the high voltage conductors could be short runs on the control module 44.

The control module 44, 126 controls the fan 20, 114 speeds and the power usage of the UV-A and UV-C LED arrays 26, 32, 38, 124. The control module 44, 126 can receive data on cabin air humidity and temperature from humidity sensors and temperature sensors commonly found in vehicle HVAC systems. This data is then used in algorithms to control the fan 20, 114 speeds and output of the UV-A and UV-C LED arrays 26, 32, 38, 124 of the system 10, 110. Alternatively, the control module 44, 126 can be an open loop set to run at a single fan 20, 114 speed and power output to the LED arrays 26, 32, 38, 124 with no input from the HVAC system. In all embodiments, the system 10, 110 can include an on/off switch that can be controlled by a user. The power usage of the system 10, 110 can range from 8 to 30 watts and is sized to the size of the cabin space it is intended to be used in.

The system 10, 110 is shown in one example as an overhead console mounted module or component kit with an output from the system that is distributed into the cabin space. There are, however, many other system configurations. Preferably the system is a stand-alone unit, however, it may be added to the post-thermal treatment side of an HVAC system. The system may discharge and disperse $H_2O_2$ in equilibrium with $H_2O$ into the cabin space to treat air and surfaces at low gas velocities and with noise levels that may range from 25 to 40 A-weighted decibel (dBA) levels.

In addition, although in the implementation shown in the Figures the system comprises three PCO elements and three UV LED arrays in series it could comprise additional numbers of PCO elements and UV-A and/or UV-C LED arrays as desired. It could be a center floor console mounted module or component kit with output distributed into the cabin space. It could be a headliner mounted and distributed output module or component kit that distributes output to the cabin space. It could be seating mounted, either beneath or in the seats, module or component kit that distributes output to the cabin space. It could be a dash or instrument panel mounted module or component kit that distributes output to the cabin space. It could be a center high mount stop lamp mounted module or component kit that distributes output to the cabin space. It could be a door trim or window regulator panel mounted module or component kit that distributes output to the cabin space. It could be a B, C or D pillar trim mounted module or component kit that distributes output to the cabin space. It could be an ambient lighting or A-cross member trim mounted module or component kit that distributes output to the cabin space. It could be a sun visor mounted module or component kit that distributes output to the cabin space. It could be a module of or a component kit that is integrated into or fed into the HVAC air inlets for full or part time output distributed into the cabin space. It could be a module in or a components kit that is integrated into a quarter trim panel and/or a trunk soft panel with output distributed to the cabin space.

In laboratory testing of an implementation of the system, the best generation of $H_2O_2$ by the surface coatings was achieved when the air humidity ranges from 5% relative humidity to 20% relative humidity, more preferably from 15% to 20% relative humidity. The preferred level of $H_2O_2$ generation is to achieve a steady state level in the cabin space of less than 50 ppb, more preferably less than 40 ppb and most preferably from 5 to 20 ppb of $H_2O_2$ in the cabin. These levels of $H_2O_2$ should provide for a 4-log reduction of pathogens in 30 minutes of treatment. A 4-log reduction means a reduction of 99.99% in 30 minutes. When the cabin air humidity is too low to permit extraction of $H_2O$ and $O_2$ from the air to generate $H_2O_2$, the LED arrays 26, 32, 38, 124 still function as time-of-flight air purifiers with respect to susceptible pathogens. In a typical vehicle such as a Chrysler Pacifica there are approximately 5,570 cubic liters of space. A simulation was conducted to determine the amount of plaque forming units (PFU) that would be generated by seven (7) large, ambulatory but Covid-19 infected males over a 10-minute period in the Pacifica cabin and then a comparison of that amount to the amount of $H_2O_2$ present at 1 ppb, which is achievable within 2 minutes with the present system. The following assumptions were utilized:

each passenger was exhaling 1000 PFU per liter per breath; a maximal tidal lung volume per person of 800 cubic centimeters (cc); an inhalation rate of 16 per minute per person; and an exhaled tidal volume of 12.8 liters per minute per person. These values yield a calculated production of 12,800 PFU exhaled per person per minute. Thus after 10 minutes each person would have exhaled 128,000 PFU for a total of 896,000 PFU in the cabin space. This yields a concentration of $2.89614 \times 10^{-22}$ in the cabin space of Covid-19. The concentration of $H_2O_2$ at 1 ppb is $1.0 \times 10^{-12}$, therefore after 10 minutes there would be a ratio of $3.45 \times 10^{12}$ $H_2O_2$ molecules for every Covid-19 virus or 3.4 trillion $H_2O_2$ per every Covid-19 virus particle, an overwhelming force to oxidize the Covid-19 viruses generated, irrespective of the kinetic oxidation rate of Covid-19 by $H_2O_2$. Taking it a step further the simulation was conducted for a Pacifica loaded with 7, non-ambulatory, intensive care level Covid-19 infected males. In this simulation the following assumptions were made: 100,000 PFU per liter of breath taken; a tidal volume of 600 cc per breath; an inhalation rate of 30 breaths per minute; an exhaled tidal volume of 18 liters per minute. This produces a PFU exhaled per person per minute of 1,800,000; a total PFU per person over the 10 minutes of 18,000,000; and total PFU in the cabin of 126,000,000 over the 10 minutes. This yields a concentration of $4.07269 \times 10^{-20}$ in the cabin space of Covid-19. Comparing this to 1 ppb of $H_2O_2$ still yields $2.46 \times 10^{10}$ or 24.6 billion $H_2O_2$ molecules per virus particle. Still an overwhelming force of $H_2O_2$ per Covid-19 virus particle.

A series of bench tests were run to determine the time required to achieve a level of 5 ppb of $H_2O_2$ in a 20-gallon test chamber at a series of relative humidity levels of the air. The temperature of the air was set at 73° Fahrenheit (F)±5 (22.7° Celsius±3); the purifier air flow rate was set at 54-56 liters per minute and the number of seconds to reach a level of 5 ppb of $H_2O_2$ was determined. The results showed that at a level of 10% relative humidity the time to reach 5 ppb was 158 seconds while at 20% relative humidity it was only 33 seconds and at 50% relative humidity it was 47 seconds. The relative humidity at each level was non-condensing. The results suggest that the best results are seen with a relative humidity of approximately 20%. During the same tests the generated ozone was determined to be less than 3 ppb. Tests in a vehicle under a variety of HVAC settings were also conducted and these showed reliable generation of 5 ppb of $H_2O_2$ within 2 minutes and with ozone levels far below those measured outside the vehicle in the ambient air.

What is claimed is:

1. A cabin purifying system for a vehicle comprising:
an air intake in communication with a fan;
a first light emitting diode array, said first light emitting diode array emitting ultraviolet C light at a wavelength of from 100 nanometers (nm) to 280 nm;
a second light emitting diode array emitting ultraviolet A light at a wavelength of from 315 nm to 400 nm;
a first photocatalytic oxidizer element having a hydrophilic surface coating comprising anatase and rutile forms of $TiO_2$ and wherein at least some of said surface coating is illuminated by said first light emitting diode array;
a second photocatalytic oxidizer element having a surface coating comprising anatase and rutile forms of $TiO_2$, said surface coating of said second photocatalytic oxidizer illuminated by said second light emitting diode array;
an air outlet, wherein said fan is configured to generate an air flow from outside said air intake to said air outlet and wherein said surface coating of said first photocatalytic oxidizer element catalyzes the conversion of $H_2O$, $O_3$ and $O_2$ in said air flow into $H_2O_2$.

2. The cabin purifying system for a vehicle according to claim 1, wherein more than 50% of the total amount of $TiO_2$ in said surface coating is in the anatase form.

3. The cabin purifying system for a vehicle according to claim 1, wherein said surface coating further comprises at least one transition metal element from the Periodic Table.

4. The cabin purifying system for a vehicle according to claim 1, wherein said first photocatalytic oxidizer element comprises at least two panels that are not parallel to each other.

5. The cabin purifying system for a vehicle according to claim 1 which includes a housing including or communicated with both the air intake and the air outlet, and in which the first light emitting diode array, the second light emitting diode array, the first photocatalytic oxidizer element and the second photocatalytic oxidizer element are arranged, and wherein the second light emitting diode array and the second photocatalytic oxidizer element are arranged downstream of both the first light emitting diode array and the first photocatalytic oxidizer element, where downstream is relative to a direction of air flow through the housing.

6. The cabin purifying system for a vehicle according to claim 5 which includes a third light emitting diode array emitting ultraviolet C light and a third photocatalytic oxidizer element having a surface coating illuminated by said third light emitting diode array, and wherein the third light emitting diode array and the third photocatalytic oxidizer element are arranged downstream of both the second light emitting diode array and the second photocatalytic oxidizer element.

7. The cabin purifying system for a vehicle according to claim 5 wherein the surface coating of the first photocatalytic oxidizer element includes a portion that makes the first photocatalytic oxidizer element more hydrophobic so that more water in the air flow reaches the second photocatalytic oxidizer element.

8. The cabin purifying system for a vehicle according to claim 1, wherein said second photocatalytic oxidizer element comprises a gridwork having multiple openings in said gridwork and wherein said gridwork is covered by said surface coating.

9. The cabin purifying system for a vehicle according to claim 8, wherein each of said openings has an inlet and an outlet relative to said air flow and wherein a diameter of said inlet of at least some of said openings is smaller than a diameter of said outlet of said at least some of said openings.

10. The cabin purifying system for a vehicle according to claim 1, wherein said second light emitting diode array is at an angle of up to 30 degrees relative to a parallel orientation to a face of said second photocatalytic oxidizer element.

11. The cabin purifying system for a vehicle according to claim 1, wherein said first and said second photocatalytic oxidizer elements are arranged in series.

12. A cabin purifying system for a vehicle comprising:
an air intake in communication with a fan;
multiple light emitting diode arrays, with at least one of said light emitting diode arrays emitting ultraviolet C light at a wavelength of from 100 nm to 280 nm and at least one of said light emitting diode arrays emitting ultraviolet A light at a wavelength of from 315 nm to 400 nm;

multiple photocatalytic oxidizer elements, each having a surface coating comprising $TiO_2$, with said surface coating of at least one of said photocatalytic oxidizer elements illuminated by at least one of said light emitting diode arrays emitting ultraviolet C light at a wavelength of from 100 nm to 280 nm and with said surface coating of at least one of said photocatalytic oxidizer elements illuminated by at least one of said light emitting diode arrays emitting ultraviolet A light at a wavelength of from 315 nm to 400 nm;
an air outlet; and
a control module, said control module controlling said fan and each of said light emitting diode arrays, wherein said fan is configured to generate an air flow into and through said air intake to and through said air outlet and wherein said surface coating illuminated by ultraviolet C light catalyzes the conversion of $H_2O$, $O_3$ and $O_2$ in said air flow into $H_2O_2$ and wherein said surface coating illuminated by ultraviolet A light catalyzes the oxidation of volatile organic compounds in said air flow.

13. The cabin purifying system for a vehicle according to claim 12, wherein said multiple photocatalytic oxidizer elements are arranged in series.

14. The cabin purifying system for a vehicle according to claim 12, wherein each of said photocatalytic oxidizer elements having a surface coating illuminated by ultraviolet C light comprises a metal substrate having said surface coating applied thereon.

15. The cabin purifying system for a vehicle according to claim 12, further comprising an ultraviolet light reflector wherein at least some of said ultraviolet light emitted by at least one of said light emitting diode arrays is reflected by said ultraviolet light reflector.

16. The cabin purifying system for a vehicle according to claim 12, wherein said surface coating comprises greater than 50% of the $TiO_2$ in an anatase form.

17. The cabin purifying system for a vehicle according to claim 12, wherein said surface coating illuminated by ultraviolet C light is hydrophilic.

18. The cabin purifying system for a vehicle according to claim 12, wherein said surface coating illuminated by ultraviolet A light is hydrophobic.

19. The cabin purifying system for a vehicle according to claim 12, wherein said control module receives inputs regarding at least one of a humidity and a temperature of air in said air flow entering said air inlet and adjusts at least one of a speed of said fan and a power output to at least one of said light emitting diode arrays based on said at least one of said humidity and said temperature.

20. The cabin purifying system for a vehicle according to claim 12, wherein said photocatalytic oxidizer element illuminated by at least one of said light emitting diode arrays emitting ultraviolet A light comprises a gridwork having a plurality of openings in said gridwork and wherein said gridwork is covered by said surface coating, and wherein each of said plurality of openings has an inlet and an outlet relative to said air flow and wherein a diameter of said inlet of at least some of said openings is smaller than a diameter of said outlet of said openings.

* * * * *